United States Patent
Shoji et al.

(10) Patent No.: US 10,191,038 B2
(45) Date of Patent: Jan. 29, 2019

(54) IMMUNOLOGICAL MEASURING METHOD AND MEASURING KIT FOR WHOLE BLOOD SAMPLE

(75) Inventors: Keiichi Shoji, Tokyo (JP); Hiroyuki Yokoi, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 0 days.

(21) Appl. No.: 14/007,412

(22) PCT Filed: Mar. 27, 2012

(86) PCT No.: PCT/JP2012/058001
§ 371 (c)(1),
(2), (4) Date: Sep. 25, 2013

(87) PCT Pub. No.: WO2012/133452
PCT Pub. Date: Oct. 4, 2012

(65) Prior Publication Data
US 2014/0017712 A1    Jan. 16, 2014

(30) Foreign Application Priority Data

Mar. 28, 2011   (JP) ................. 2011-070872

(51) Int. Cl.
*G01N 33/543*   (2006.01)
*G01N 33/53*   (2006.01)

(52) U.S. Cl.
CPC ... *G01N 33/5306* (2013.01); *G01N 33/54333* (2013.01); *G01N 33/54393* (2013.01); *G01N 2333/4737* (2013.01)

(58) Field of Classification Search
CPC ............ G01N 33/536; G01N 33/5306; G01N 33/54333; G01N 33/54393; G01N 2333/4737
See application file for complete search history.

(56) References Cited

U.S. PATENT DOCUMENTS

| | | | |
|---|---|---|---|
| 4,098,876 A * | 7/1978 | Piasio | G01N 33/538 436/500 |
| 4,743,542 A * | 5/1988 | Graham et al. | 435/7.94 |
| 5,451,504 A * | 9/1995 | Fitzpatrick | G01N 33/558 435/7.2 |
| 5,486,479 A | 1/1996 | Ito et al. | |
| 5,506,151 A | 4/1996 | Ito et al. | |
| 5,814,220 A | 9/1998 | Mikami et al. | |
| 2003/0113235 A1 | 6/2003 | Yoko et al. | |
| 2004/0048397 A1 | 3/2004 | Yokoi | |
| 2006/0286679 A1 | 12/2006 | Ono et al. | |
| 2007/0106067 A1 * | 5/2007 | Furusako | C07K 14/70596 530/388.22 |
| 2009/0117596 A1 * | 5/2009 | Hashimoto | G01N 33/56911 435/7.32 |

FOREIGN PATENT DOCUMENTS

| | | | |
|---|---|---|---|
| CN | 1111016 A | 11/1995 | |
| EP | 410645 A2 * | 1/1991 | ............. G01N 35/02 |
| EP | 1 650 570 A1 | 4/2006 | |
| JP | 7-301632 | 11/1995 | |
| JP | 08-201391 A | 8/1996 | |
| JP | 9-171013 | 6/1997 | |
| JP | 2000-146970 A | 5/2000 | |
| JP | 2004-191332 A | 7/2004 | |
| JP | 2006-162466 A | 6/2006 | |
| WO | WO 9843067 A1 * | 10/1998 | ....... G01N 33/54326 |
| WO | WO 9858259 A1 * | 12/1998 | ............. G01N 3/543 |
| WO | WO 9964447 A1 * | 12/1999 | ............... C07K 7/04 |
| WO | 01/84152 A1 | 11/2001 | |
| WO | 02/073203 A1 | 9/2002 | |
| WO | 2004/106930 A1 | 12/2004 | |
| WO | WO 2008033164 A1 * | 3/2008 | ............. G01N 33/80 |

OTHER PUBLICATIONS

International Search Report, dated May 1, 2012, PCT application No. PCT/JP2012/058001, 2 pages.

* cited by examiner

*Primary Examiner* — Andrea S Grossman
(74) *Attorney, Agent, or Firm* — Kilpatrick Townsend & Stockton LLP

(57) ABSTRACT

In a known method of measuring a target substance, comprising: providing a sample solution containing the target substance, a first reaction solution, and a second reaction solution; sequentially aspirating the sample solution and the first reaction solution, using a measuring apparatus equipped with a dispensing unit, into the dispensing unit; discharging them at a time from the dispensing unit, to bring them into contact with the second reaction solution, and to form a complex of the target substance and a first partner which is contained in at least one of the first reaction solution or the second reaction solution and reacts specifically with the target substance; and analyzing the resulting complex, an improved method capable of inhibiting a reaction which adversely affects measurement results is provided. In this improved method, the specific gravity of the sample solution is different from the specific gravity of the first reaction solution; and the sample solution and the first reaction solution are aspirated into the dispensing unit in an overlaid state.

12 Claims, 3 Drawing Sheets

Aspiration  Aspiration (1) (2) (3) (4) (5) (6) (7) (8) (9) (10)　(11) (12) (13)　(14)

IMMUNOLOGICAL MEASURING METHOD AND MEASURING KIT FOR WHOLE BLOOD SAMPLE

CROSS-REFERENCE TO RELATED APPLICATIONS

This application is a national phase application under 35 U.S.C. 371 claiming priority to PCT/JP2012/058001, filed Mar. 27, 2012, which application claims priority to JP 2011-070872, filed Mar. 28, 2011, the teachings of which are hereby incorporated by reference in their entireties for all purposes.

TECHNICAL FIELD

The present invention relates to a measuring method and kit of which the subject is a target substance (such as a trace component or the like) contained in a sample. More particularly, the present invention relates to an immunological analysis method and an immunological analysis kit of which the subject is a target substance (such as a trace component or the like) contained in a whole blood sample.

BACKGROUND ART

As a method of measuring a target substance (a trace component or the like) contained in a biological sample, an immunological measuring method utilizing an antigen-antibody reaction is widely used, and radioimmunoassay (RIA), enzyme-linked immunosorbent assay (ELISA), or the like are known. Recently, serum or plasma is used as a sample in many cases, but a measuring method in which whole blood can be measured without pretreatment is desired due to pretreatment hassle. However, since a whole blood sample contains not only a trace component or the like as a subject to be measured, but also many contaminants (non-target substances), it cannot be carried out in the same manner as conditions using serum samples or plasma samples in many cases. In order to improve the reaction precision, it has been reported, as shown in Patent literature 1, that prozone can be avoided by adding a reaction inhibitor (a free antibody or its fragment capable of competing with an antibody immobilized on a solid phase or a labeling substance) in a reaction. In this case, a plurality of reaction substances co-exist in a single measurement, and therefore, it is difficult to construct a measurement system.

Further, as a technique capable of conveniently examining a plurality of samples, various automated immunologically measuring apparatus are known, such as an automated measuring apparatus capable of simultaneously measuring a plurality of samples, as shown in Patent literature 2. It is disclosed that, in this automated measuring apparatus, samples containing a target substance are dispensed into a cartridge having a dilution well where a predetermined sample amount is diluted into a desired dilution rate, a reaction well where a target substance contained in the samples is reacted with a substance which specifically reacts with it, and a storage well containing reaction components or the like; the samples are diluted to desired dilution rates on the cartridge; the target substance contained in the diluted samples is reacted with the substance which specifically reacts with the target; and the amount of the resulting reaction product is measured, to conveniently measure a plurality of target substances with different dilution rates contained in the samples. It is also disclosed that the apparatus has an aspirating and discharging unit, and the dispensing step and measurement are carried out using this unit.

On the other hand, as a method of measuring a whole blood sample as a subject, a method in which a surfactant is contained to avoid the effects of components contained in whole blood samples is disclosed, as shown in Patent literature 3. However, in the measuring method in which each reaction reagent is sequentially dispensed to carry out reactions, it is not known that the divergence between plasma and whole blood derived from the same sample is observed, and a method to solve such problems has not been proposed.

CITATION LIST

Patent Literature

[Patent literature 1] Japanese Unexamined Patent Publication (Kokai) No. 2004-191332
[Patent literature 2] WO2001/084152
[Patent literature 3] WO2002/073203

SUMMARY OF INVENTION

Technical Problem

As it will be concretely explained in the Examples below, the present inventors found that, in a method of measuring a target substance using a sample or its processing solution (hereinafter referred to as the sample solution) containing a target substance, a partner which specifically reacts with the target substance and which forms an immunocomplex with the target substance formed in the main reaction (for example, an antibody (the first reaction solution contains an antibody labeled with alkaline phosphatase, and the second reaction solution contains an antibody immobilized on magnetic particles)), and a free antibody which specifically reacts with the target substance and which can inhibit the formation of the immunocomplex (the free antibody is added to the first and second reaction solutions), when a whole blood sample as an analyte was measured using an automated enzyme immunoassay analyzer equipped with a dispensing unit, and when the sample solution containing a target substance was aspirated using the dispensing unit, and then, the first reaction solution was further aspirated, the divergence between the plasma sample and the whole blood sample derived from the same sample was observed, because the antibody, which would react as a reaction inhibitor to inhibit the formation of immunocomplex in the main reaction, reacted with the target substance contained in the whole blood sample prior to the main reaction.

The present invention was made to solve this problem, and an object of the present invention is to provide a measuring method and kit capable of inhibiting a reaction which adversely affects measurement results, by using a measuring apparatus equipped with a dispensing unit, to start the reaction between a sample containing a target substance and a partner which specifically reacts with the target substance, substantially at the main reaction.

Solution to Problem

Under these circumstances, the present inventors had intensive studies, and as a result, found that, in a method of measuring a target substance using a measuring apparatus equipped with a dispensing unit, and using a sample solution containing a target substance, the first reaction solution, and the second reaction solution, the progress of an undesired reaction prior to the main reaction could be inhibited, and therefore, the divergence between the plasma sample and the whole blood sample derived from the same sample could be avoided, by using a method characterized in that at least one of the first reaction solution and the second reaction solution contained the first partner which specifically reacted with the target substance and which formed a complex with the target substance formed in the main reaction, and the sample solution containing the target substance and the first reaction solution were present in specific gravity different from each other, in a flow path in the dispensing unit. The present invention was completed on the basis of these findings, as a method of conveniently and accurately measuring a target substance contained in a sample, regardless of the sample type.

The present invention relates to the following inventions:

[1] A method of measuring a target substance, comprising the steps of:

providing a sample suspected of containing the target substance, or a solution derived from the sample, a first reaction solution, and a second reaction solution;

aspirating the sample or the solution derived therefrom, and the first reaction solution, using a measuring apparatus equipped with a dispensing unit, sequentially in this order or the reverse order, into the dispensing unit;

discharging them at a time from the dispensing unit, to bring them into contact with the second reaction solution, and to form a complex of the target substance and a first partner which is contained in at least one of the first reaction solution or the second reaction solution and reacts specifically with the target substance; and analyzing the resulting complex, or a signal derived from the complex, said method being characterized in that:

the specific gravity of the sample or the solution derived therefrom is different from the specific gravity of the first reaction solution; and the sample or the solution derived therefrom and the first reaction solution are aspirated into the dispensing unit in an overlaid state.

[2] The method of [1], wherein the sample is whole blood.

[3] The method of [1] or [2], wherein the specific gravity of the first reaction solution is higher than the specific gravity of the sample or the solution derived therefrom, and the sample or the solution derived therefrom, and the first reaction solution are aspirated into the dispensing unit in this order.

[4] The method of any one of [1] to [3], wherein the first reaction solution contains at least one substance selected from the group consisting of polyhydric alcohols, sugar alcohols, and sugars.

[5] The method of [4], wherein the first reaction solution contains at least one substance selected from the group consisting of ethylene glycol, propylene glycol, diethylene glycol, glycerol, pentose, hexose, triose, tetrose, heptose, sucrose, trehalose, isotrehalose, kojibiose, sophorose, nigerose, laminaribiose, maltose, cellobiose, isomaltose, gentiobiose, lactose, turanose, maltulose, palatinose, gentiobiulose, mannobiose, melibiose, melibiulose, neolactose, galactosucrose, scillabiose, rutinose, rutinulose, xylobiose, primellose, oligosaccharides, raffinose, melezitose, and maltotriose.

[6] The method of [4] or [5], wherein one or more substances described in [4] or [5] are included in the first reaction solution in an amount of 10% to 30% as the total amount thereof.

[7] The method of any one of [1] to [6], wherein the first partner which reacts specifically with the target substance is an antibody or an antigen.

[8] The method of any one of [1] to [7], wherein the first partner which reacts specifically with the target substance is contained in the first reaction solution, and a second partner which recognizes a region different from a region recognized by the first partner and reacts specifically with the target substance is contained in the second reaction solution.

[9] The method of [8], wherein the first and second partners which react specifically with the target substance is labeled with a labeling substance, or immobilized on a solid-phase carrier.

[10] The method of [9], wherein the first partner which is contained in the first reaction solution and reacts specifically with the target substance is labeled with a labeling substance, and the second partner which is contained in the second reaction solution and reacts specifically with the target substance is immobilized on a solid-phase carrier.

[11] The method of any one of [1] to [10], wherein at least one of the first reaction solution or the second reaction solution contains a third partner which inhibits the formation of the complex with the target substance and reacts specifically with the target substance.

[12] The method of [11], wherein the first reaction solution and the second reaction solution contain the third partner which reacts specifically with the target substance.

[13] The method of [11] or [12], wherein the third partner which reacts specifically with the target substance is an antibody or an antigen.

[14] The method of any one of [1] to [13], wherein the dispensing unit is a tip.

[15] A kit for measuring a target substance, which is used in a measuring apparatus equipped with a dispensing unit, wherein the kit comprises a first reaction solution and a second reaction solution;

at least one of the first reaction solution and the second reaction solution contains a first partner which reacts specifically with the target substance;

the measuring apparatus carries out a step of aspirating a sample or a solution derived from the sample, and the first reaction solution, sequentially in this order or the reverse order, into the dispensing unit; and the specific gravity of the sample or the solution derived therefrom is different from the specific gravity of the first reaction solution.

[16] The measuring kit of [15], the specific gravity of the first reaction solution is higher than the specific gravity of the sample or the solution derived therefrom.

The terms "first partner" and "second partner" as used herein mean substances which specifically react with a target substance and form a complex with the target substance, said complex being formed in the main reaction. The term "third partner" as used herein means a substance which specifically reacts with a target substance and inhibits the formation of a complex with the target substance, said complex being formed in the main reaction.

Advantageous Effects of Invention

By using the method of the present invention, it is possible to conveniently and accurately measure a target substance contained in a sample, regardless the sample type. In particular, even when a whole blood sample having different properties from other samples is used, the target substance can be measured without divergence to the value of a serum sample or a plasma sample, which is generally used for comparison.

DESCRIPTION OF EMBODIMENTS

Figure 1:
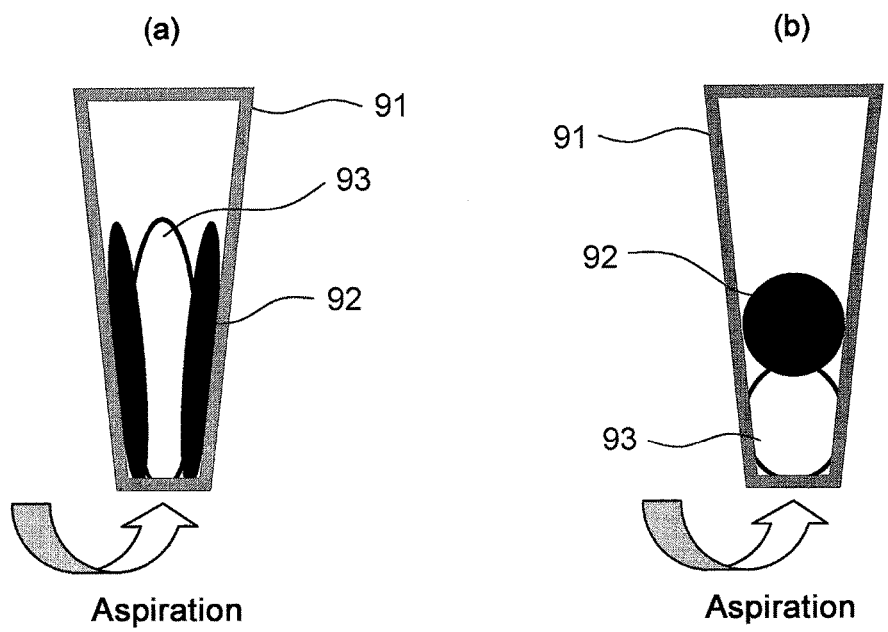
FIG. 1 schematically shows the state of whole blood (sample solution; 92) and a first reaction solution (labeled antibody solution; 93) in a tip (91) as a dispensing unit when these solutions are aspirated into the tip. (a) is a case where the first reaction solution does not contain a sugar, and (b) is a case where the first reaction solution does contain a sugar.

1. Automated Measuring Apparatus and Measuring Method

The method of the present invention may be applied to an automated measuring apparatus equipped with a dispensing unit and a measuring method. As the dispensing unit, for example, a method utilizing a random access, such as Japanese Translation Publication (Kohyo) No. 09-503060, or a method utilizing a uniform operation, such as WO2001/084152, may be used. As the measuring method, known immunoassays, such as chemiluminescent enzyme immunoassay (CLEIA) or turbidimetric immunoassay, may be used. Chemiluminescent enzyme immunoassay (CLEIA) may be used as enzyme-linked immunosorbent assay (sometimes referred to as enzyme immunoassay) (ELISA). Sandwich ELISA is often used for a high-sensitivity analysis.

Hereinafter, embodiments of known automated measuring apparatus and measuring methods which may be used in the measuring method and the kit of the present invention will be exemplified, but the present invention is not limited to the embodiments.

The automated measuring apparatus for measurement comprises, at least, a cartridge holder capable of holding a cartridge for measurement, a dispensing unit which dispenses reagents and/or samples to the cartridge held in the cartridge holder, and a measuring unit for measuring a reaction product in the cartridge held in the cartridge holder. The cartridge holder may be a commonly-used cartridge holder, so long as it has a structure capable of holding a cartridge for measurement.

The dispensing unit comprises general components, such as a unit for aspirating and discharging liquid, in accordance with the type and properties of reagents and/or samples. The term "dispense" as used herein includes to transfer reagents and/or samples from the outside of a cartridge to a well of the cartridge, and to transfer reagents and/or samples from a well to another well on the cartridge.

The measuring unit comprises general components, such as a photometric measurement unit, in accordance with the type and properties of a reaction product.

As the cartridge for measurement, for example, a cartridge in which two or more lines of well groups are arranged, a single cartridge in which one line of wells are arranged, or a combination of these cartridges may be used. When a measurement is carried out using a plurality of cartridges, the apparatus has a plurality of units for carrying out a series of immune reactions, and a plurality of units for simultaneously controlling the steps of dispensing of samples, dilution of samples, dispensing of reagents, B/F separation, photometric measurement, and the like. In this way, even in the case of immunoassay, a plurality of items can be simultaneously measured using an apparatus for carrying out only a single-style analyzing step, without a significantly increased time needed for measurement even if the analysis items are different.

The cartridge for measurement has a dispensing well for dispensing samples, a dilution well for diluting a desired amount of samples to a desired dilution rate, a reaction well for reacting a target substance in samples with a substance which specifically reacts with the target substance, a washing well for B/F separation corresponding to the reaction well, a reagent storage well for storing reagents needed for the measurement of a target substance contained in samples, a measuring well for measuring the amount of a reaction product, and the like. As the measuring well, a photometric measuring well may be used for an optical measurement. It is not necessary to arrange all the wells in the single cartridge for measurement, and appropriate cartridges can be selected in accordance with the apparatus used. For example, reagents needed for the measurement of a target substance contained in samples may be stored in another cartridge for providing reagents. Each well is not limited to only its purpose for use and, for example, the dispensing well may also be used for a dilution well, and the reagent storage well may also be used for a reaction well. The number of each well may be appropriately selected.

In the reaction well, part of reagents which participate in reactions may be stored. In the reagent storing well or the reaction well, a single reagent may be stored, or a plurality of reagents may be stored so long as the regents stored do not react with each other. The reagents stored may be in a liquid form (such as a solution or a suspension), or may be in a solid form so long as it can be dissolved or suspended in a liquid to be poured into wells.

When reagents, solutions, and/or the like, such as a dilution solution, a labeling substance, a washing solution, or the like, are stored in the cartridge for measurement, it is preferable to seal the top of the cartridge with aluminum foil, plastic film, or the like, in order to avoid evaporation and degradation of reagents or the like, and contamination. In particular, sealing with aluminum foil is preferable, because it can be automatically and easily opened using a perforation unit of an automated measuring apparatus. When reagents, solutions, and/or the like are stored in another cartridge and a measurement is carried out using these cartridges, it is preferable to seal this cartridge.

On the cartridge for measurement, a bar code which records information about samples, information about analysis items, reagent management information, and the like may be attached by printing, sticking, or the like. By attaching such a bar code on the cartridge, when an automated measuring apparatus capable of recognizing the bar code on the cartridge and capable of automatically selecting analysis items is used, the operator can conveniently and efficiently measure desired analysis items using the single automated measuring apparatus, only by selecting an appropriate cartridge. Further, it is not necessary to carry out a worksheet operation, which is carried out in a conventional automated measuring apparatus and causes erroneous setting of analysis items, and therefore, a plurality of analysis items may be conveniently measured without failure. Furthermore, storage and management of reagents may be convenient.

In the automated measuring apparatus which is used by incorporating thereinto the cartridge for measurement, known units may be used as, for example, a unit for aspirating a predetermined amount of liquid from a well and discharging it to another well, a unit for stirring the content in a well, a unit for B/F separation, a unit for measuring the amount of a reaction product or a labeling substance, a unit for calculating the amount of a target substance from the measurement results of a reaction product or a labeling substance, a unit for regulating the temperature of the cartridge, a unit for recognizing a bar code, a unit for simultaneously measuring a plurality of cartridges, and the like.

Hereinafter, the present invention will be further explained on the basis of a preferred embodiment, a measurement using immunoassay, in particular, chemiluminescent enzyme immunoassay (CLEIA).

A cartridge as a preferred embodiment is a cartridge for automated measurement which is used by incorporating it into an automated measuring apparatus capable of automatically quantifying a target substance contained in samples, and which has a reaction well for reacting a target substance with a substance which specifically reacts with the target substance, a plurality of reagent storing wells for storing reagents used for reactions, a dispensing well for dispensing samples, a dilution well for diluting samples, a washing well for B/F separation, and/or a photometric measuring well. As described above, the reagent storing wells may also be used as a reaction well. Preferably, a certain amount of dilution solution for diluting a predetermined amount of sample to a desired dilution rate is stored in the dilution well; a solid-phase carrier for carrying out an immunologically specific reaction, a labeled antigen or antibody, a reagent for measuring the labeling substance amount, and the like are individually stored in the plural reagent storing wells; and a washing solution for washing an immunocomplex is stored in the washing well. The reagent storage wells of the cartridge may also be used as reaction wells by, for example, storing an antigen (or antibody)-bound solid-phase carrier (sensitized solid-phase) in the wells.

As the solid-phase carrier, for example, polystyrene beads, magnetic particles, latex particles, or the like, which are conventionally used in immunoassay, may be used. Further, instead of the addition of such a solid-phase carrier, an antibody or antigen may be immobilized on the inner wall of the well, and may be used.

As the immunoassay used in this embodiment, chemiluminescent enzyme immunoassay (CLEIA) advantageous in terms of sensitivity is preferable, and as the solid-phase carrier, magnetic particles capable of conveniently carrying out B/F separation, which is essential in chemiluminescent enzyme immunoassay (CLEIA), using a magnet is preferable. This B/F separation may be carried out by applying a magnetic field with, for example, a permanent magnet, an electromagnet, or the like from the outside of cartridge. It may also be carried out by a magnet arranged at the side of an aspirating and discharging unit of a dispensing unit such as a pipette tip or the like, as shown in JP11-262678A.

Other reagent storing wells may also be used as reaction wells by adding a labeled antigen or antibody. Examples of the labeling substance include enzymes, radioisotopes, coloring substances, fluorescent substances, luminescent substances, and various colored particles. Enzymes are preferably used in chemiluminescent enzyme immunoassay (CLEIA). Examples of a labeling enzyme include alkaline phosphatase, peroxidase, galactosidase, and glucooxidase. As the substrate for the labeling enzyme, a substrate corresponding to each enzyme may be used. For example, adamantyl methoxyphenyl phosphoryl dioxy cetane (AMPPD) or CDP-Star (registered trademark) for alkaline phosphatase, luminol/peroxide for peroxidase, and adamantyl methoxyphenyl $\beta$-D-galactosyl dioxetane (AMPGD) for galactosidase, may be used.

The measurement of the labeling substance may be carried out, for example, in chemiluminescent enzyme immunoassay, by mixing an immunocomplex with a substrate for the labeling enzyme, and directly measuring luminescence from the measuring well using a photo multiplier tube or the like. In the case of enzyme immunoassay, it may be carried out by mixing it with an enzyme substrate solution, irradiating it with a measurement light at a measuring wavelength from the bottom or the side of the measuring well, and measuring the transmitted light which has passed through the measuring well.

With respect to the dispensing unit, it is preferable that a flow path in the dispensing unit, i.e., the portion which is brought into contact with reagents and/or samples, is exchangeable. As the dispensing unit, a tapered form capable of easily aspirating and discharging reagents or samples, more particularly, tips or the like, may be used. It is preferable that this portion is exchanged for each measurement, because it becomes easy to avoid contamination of the cartridge to be used for the next measurement.

2. Measuring Method of the Present Invention

The measuring method of the present invention may be carried out with reference to known automated measuring apparatus and measuring methods. Hereinafter, the main features of the present invention will be explained in detail.

The measuring method of the present invention is based on the concept that when a measuring apparatus equipped with a dispensing unit is used, a reaction which adversely affects measurement results is inhibited, so that the reaction of a sample solution containing a target substance with a partner which specifically reacts with the target substance can substantially start in the main reaction.

More particularly, in a method of measuring a target substance using a sample solution containing the target substance, a first reaction solution, and a second reaction solution, and a measuring apparatus equipped with a dispersing unit, at least one of the first reaction solution and a second reaction solution contains a first partner which specifically reacts with the target substance and forms a complex with the target substance in the main reaction, and the sample solution containing the target substance and the first reaction solution can be present in specific gravity different from each other, in a flow path of the dispersing unit.

In the case of a general automated measuring apparatus, a sample is initially aspirated in many cases. That is to say, the first step of aspirating a sample solution containing a target substance using a dispensing unit (for example, a tip) is carried out, and the second step of aspirating the first reaction solution using the dispensing unit is carried out. In this case, as shown in FIG. 1, when the specific gravity of the sample solution (92) is higher than that of the first reaction solution (93), for example, the sample solution falls along the wall of the tip (91), and as a result, the contacting surface between the sample solution and the first reaction solution is increased, and an undesired reaction proceeds before the main reaction. Which specific gravity is adjusted between the sample and the first reaction solution may be appropriately selected. Since it is easy to increase specific gravity, it is preferable to increase the specific gravity of the first reaction solution. By increasing the specific gravity of the first reaction solution in comparison with that of the sample solution, the first reaction solution can be layered under the sample solution layer in the flow path of the dispensing unit in a state that these layers are substantially immiscible, and an undesired reaction proceeds before the main reaction, and therefore, it is preferable.

The sample used in the present invention is not limited, so long as it contains or is suspected of containing a target substance. Examples of the sample include whole blood, serum, plasma, and urine.

In particular, when the sample is whole blood, since the sample solution generally has a specific gravity higher than that of a general reaction solution, it often causes an undesired reaction which affects the measurement. Therefore, it is most preferable to increase the specific gravity of the first reaction solution, when the sample is whole blood. Since a serum sample or a plasma sample generally has a specific gravity similar to that of a general dilution solution, it sometimes does not affect the measurement. However, since there is a possibility that it may cause a problem when a measurement with high sensitivity or high precision is carried out, it is preferable to increase the specific gravity of the first reaction solution in comparison with the sample solution, when samples other than whole blood are used. Further, since various types of samples are simultaneously measured in many cases, it is preferable to increase the specific gravity of the first reaction solution in comparison with the sample solution.

For example, with respect to the specific gravity of the whole blood sample solution, the specific gravity of the first reaction solution may be different therefrom by 0.05% to 10%, preferably 0.1% to 7.5%, and more preferably 0.1% to 3%. Specific gravity may be easily measured using a known specific gravity meter or the like.

So long as the sample solution and the first reaction solution having a specific gravity different from each other may be prepared, any substance may be used, but it is necessary to select a substance in which components contained in the sample, the first reaction solution, and the second reaction solution may be simultaneously mixed in the main reaction, and the substance does not adversely affect the measurement. For example, a substance which does not destroy blood cell components is preferable. More particularly, polyhydric alcohols, sugar alcohols, or sugars may be used. As the polyhydric alcohols, ethylene glycol, propylene glycol, or diethylene glycol may be used. As the sugar alcohols, glycerol may be used. The sugars are most preferable, because it can increase the specific gravity without affecting the components of the reaction solutions and various samples. As the sugars, monosaccharides, disaccharides, and trisaccharides may be used. Examples of the monosaccharides include pentose, hexose, triose, tetrose, and heptose. Examples of the disaccharides include sucrose, trehalose, isotrehalose, kojibiose, sophorose, nigerose, laminaribiose, maltose, cellobiose, isomaltose, gentiobiose, lactose, turanose, maltulose, palatinose, gentiobiulose, mannobiose, melibiose, melibiulose, neolactose, galactosucrose, scillabiose, rutinose, rutinulose, xylobiose, and primellose. Examples of the trisaccharides include oligosaccharides, raffinose, melezitose, and maltotriose. Disaccharides and trisaccharides are preferable, and sucrose is most preferable. Preferable concentration of the sugar used may be appropriately selected in accordance with its properties. The total concentration contained in the first reaction solution and the second reaction solution may be, for example, 10% to 30%, preferably 10% to 20%, more preferably 10% to 15%. As another embodiment, 15% to 30% is preferable.

As the steps for measurement, the method of the present invention comprises the first step of aspirating a sample solution containing a target substance using a dispensing unit, the second step of further aspirating the first reaction solution using the dispensing unit, the third step of discharging the sample solution and the first reaction solution to a reaction well to react them with the second reaction solution, and the fourth step of measuring the amount of a reaction product. Prior to the first step, for example, a step of dispensing a sample containing a target substance to a dispensing well, a step of diluting a sample in a dilution well, and the like may be included. Further, between the third step and the fourth step, a step of carrying out B/F separation of a complex with a substance which specifically binds to a target substance may be included.

A dilution rate of a sample, and a dilution solution with which a dilution well is filled may be appropriately selected in accordance with the type of sample, target substance, substance which specifically reacts with the target substance, and the like. The dilution solution may contain a reagent necessary for pretreatment of a sample. In this case, dilution and pretreatment are carried out simultaneously in a dilution well.

As the reagent necessary for pretreatment of a sample, for example, an acid, an alkali, an organic solvent, a protein denaturing agent, a surfactant or the like may be used. A sample may be pretreated by adding these agents in the sample dilution step. When whole blood is used as a sample, it is preferable that pretreatment is carried out by adding a surfactant or the like, because many contaminants are contained in whole blood. By simultaneously carrying out the dilution and the pretreatment of a sample, even when whole blood or the like is used as a sample, a convenient measurement with high accuracy may be carried out, and it may be preferably used for, for example, an emergency test, or a point-of-care testing (POCT) or the like performed by a doctor or a nurse.

The sample solution as used herein means a sample per se collected from a patient, or a sample solution prepared by diluting a sample from a patient with a dilution solution and/or pretreating the same.

The target substance in the present invention is not limited, so long as a partner which specifically reacts with the target substance is present. As a combination of the target substance and its partner which specifically reacts with it, for example, an antigen and an antibody, an antibody and an antigen, a sugar chain and lectin or the like may be used. The term "specifically react" as used herein means to bind biochemically and specifically. The target substance and its partner which specifically reacts with it may change in their chemical properties before and after the binding, like a substrate.

The conditions or the like of the step of reacting the target substance with its partner which specifically reacts with it, and the step of measuring the amount of the reaction product may be appropriately selected in accordance with the combination of the target substance and its partner which specifically reacts with it. For example, the reaction of an enzyme with its substrate and the measurement of the amount of the reaction product may be carried out by reacting the enzyme with the substrate by mixing them and measuring the amount of the reaction product (decomposition product of the substrate). The reaction of an antigen with an antibody and the measurement of the amount of the reaction product may be carried out by forming a reaction product (immunocomplex) by mixing an antibody or antigen with a labeling substance and a solid carrier immobilized with its antibody or antigen, removing (B/F separation) the unreacted antibody or antigen and labeling substance from the immunocomplex by washing, and measuring the amount of the labeling substance which binds to the solid phase by the formation of immunocomplex. The term "measuring the amount of a reaction product" as used herein includes not only to directly measure the amount of the reaction product per se, but also to measure a signal or the amount of a substance which quantitatively relates to the amount of the reaction product. The amount of the target substance contained in a sample may be calculated from the amount of the reaction product measured.

In connection with this, the term "immunocomplex" as used herein means a product generally formed by binding the target substance with its partner which specifically reacts with it.

It is preferable that the reaction between the target substance and its partner which specifically reacts with it is an immunological reaction. That is to say, the target substance and its partner which specifically reacts with it is preferably an antibody or an antigen. The immunological reaction is preferably a reaction in which a target substance contained in a sample is reacted with the first partner which immunologically and specifically reacts with the target substance to form the first immunocomplex, and the first immunocomplex is reacted with the labeled second partner which immunologically and specifically reacts with it to form the second immunocomplex. It is more preferable that the target substance is an antigen, and its partner which specifically reacts with it is an antibody.

The partner which specifically reacts with a target substance in the present invention (preferably the combination of the first partner and the second partner) means a substance which constitutes a complex which generates a signal to be measured as the amount of the target substance.

The main reaction as used herein means a reaction in which a target substance is reacted with its partner which specifically reacts with it to form a complex. That is to say, it means a reaction of a target substance with a substance which constitutes a complex which generates a signal to be measured as the amount of the target substance.

The term "substantially start a reaction at the main reaction" as used herein means substances which contribute to the main reaction are present in the measurement system before the main reaction, to the extent there is no negative effects on the measurement result, and the main reaction starts by bringing them into contact with each other at the beginning of the main reaction.

The reaction solution used in the present invention is a solution which reacts with a target substance. The reaction solution can contain substances necessary for the main reaction. As the reaction solution, at least two reaction solutions are used in the present invention.

The partner which specifically reacts with a target substance in the present invention may be contained in at least one of the first and second reaction solutions. It is most preferable when one kind of partner is used, for example, in the case of a latex agglutination method using one kind of antibody.

Further, the first partner which specifically reacts with a target substance may be contained in both the first and second reaction solutions. It is most preferable when two or more partners, i.e., the combination of the first and second partners, are used. Further, it is preferable that the first partner which is contained in the first reaction solution and which specifically reacts with the target substance, and the second partner which is contained in the second reaction solution and which specifically reacts with the target substance react with different regions of the target substance. For example, a sandwich ELISA method using two or more antibodies may be exemplified.

The partner which specifically reacts with a target substance may be a partner labeled with a labeling substance, or a partner immobilized on a solid-phase carrier. For example, a latex agglutination method using latex particles on which one kind of antibody is immobilized may be exemplified.

The first partner which is contained in the first reaction solution and which specifically reacts with a target substance may be a partner labeled with a labeling substance, and the second partner which is contained in the second reaction solution and which specifically reacts with a target substance may be a partner which is immobilized on a solid-phase carrier. For example, a sandwich ELISA method in which one antibody is immobilized on magnetic particles, and another antibody is labeled with a labeling substance may be exemplified.

The third partner which specifically reacts with a target substance in the present invention means a substance which inhibits the formation of a complex which generates a signal to be measured as the amount of the target substance. The third partner is not limited, so long as it inhibits the formation of the complex, and does not form the complex. For example, when the target substance is an antigen, and the first and/or second partners are antibodies, a substance which competitively inhibits the binding between the antigen and the antibody may be exemplified. As the substance which competitively inhibits the binding between the antigen and the antibody, an antibody having the same epitope as that of the antibody may be exemplified.

More particularly, when one antibody having the same epitope against a certain antigen is immobilized on magnetic particles (the first partner which specifically reacts with a target substance, and another antibody having the same epitope against the antigen is provided as a free antibody (third partner which specifically reacts with the target substance), and an antibody which is labeled for detection and has a different epitope is provided (second partner which specifically reacts with the target substance), and these antibodies are applied to the main reaction together with a certain antigen, a competitive reaction between the immobilized antibody and the free antibody occurs, the antibody immobilized under the optimal conditions for measurement binds to the antigen, and the labeled antibody further binds thereto, and an immunocomplex of the immobilized antibody, the antigen, and the labeled antibody which preferably reflects the amount of the target substance is formed.

In the case of such a measuring method using the third partner which inhibits the formation of immunocomplex, it is most preferable because the first and/or the second partners which specifically react with the target substance and the third partner which specifically reacts with the target substance can simultaneously begin to react with the target substance at the main reaction, and therefore, the precision in measuring the target substance becomes high.

More particularly, at least one of the first and second reaction solutions can contain the third partner which specifically reacts with the target substance and which inhibits the formation of immunocomplex with the target substance formed in the main reaction. Further, both the first and second reaction solutions can contain the third partner which specifically reacts with the target substance and which inhibits the formation of immunocomplex with the target substance formed in the main reaction.

When a sealed cartridge or the like is used, scattering of the contents or aspiration failures occurs due to the movement of units or the impact of seal destruction, and the reaction solution cannot be accurately aspirated in some cases. Therefore, it is preferable that both the first and second reaction solutions contain the third partner which specifically reacts with the target substance and which inhibits the formation of immunocomplex with the target substance formed in the main reaction, because a big change in composition does not occur in the main reaction.

3. Kit of the Present Invention

The kit of the present invention may be used for the measuring method of the present invention. More particularly, the kit comprises the first reaction solution having a specific gravity different from that of a sample solution containing a target substance, and the second reaction solution, and at least one of the first and second reaction solutions contain the first partner which specifically reacts with the target substance. It is preferable that the specific gravity of the first reaction solution is higher than that of the sample solution.

4. Embodiments of the Present Invention

As the first embodiment of the present invention, a turbidimetric immunoassay of an antigen, using a measuring apparatus equipped with a dispensing unit, using a whole blood sample solution containing a target substance (antigen), the first reaction solution, and the second reaction solution containing an antibody which is immobilized on latex particles and which specifically reacts with the antigen, is exemplified. More particularly, the first step of aspirating the sample solution using the dispensing unit, and the second step of aspirating the first reaction solution using the dispensing unit may be carried out, to layer the first reaction solution under the sample solution layer; the sample solution and the first reaction solution aspirated using the dispensing unit may be discharged to the second reaction solution to carry out the main reaction; and the amount of antigen may be measured by optically measuring latex agglutination.

As the second embodiment of the present invention, a turbidimetric immunoassay of an antigen, using a measuring apparatus equipped with a dispensing unit, using a whole blood sample solution containing a target substance (antigen), the first reaction solution comprising a free antibody which inhibits the formation of immunocomplex in the main reaction and which specifically reacts with the antigen, and the second reaction solution containing an antibody which is immobilized on latex particles and which specifically reacts with the antigen, is exemplified. More particularly, the first step of aspirating the sample solution using the dispensing unit, and the second step of aspirating the first reaction solution using the dispensing unit may be carried out, to layer the first reaction solution under the sample solution layer; the sample solution and the first reaction solution aspirated using the dispensing unit may be discharged to the second reaction solution to carry out the main reaction; and the amount of antigen may be measured by optically measuring latex agglutination. In the main reaction, a competitive reaction between the immobilized antibody and the free antibody occurs against the antigen.

As the third embodiment of the present invention, a sandwich ELISA method of an antigen, using a measuring apparatus equipped with a dispensing unit, using a whole blood sample solution containing a target substance (antigen), the first reaction solution containing an antibody labeled with alkaline phosphatase, and the second solution containing an antibody which is immobilized on magnetic particles and which specifically reacts with the antigen, is exemplified. More particularly, the first step of aspirating the sample solution using the dispensing unit, and the second step of aspirating the first reaction solution using the dispensing unit may be carried out, to layer the first reaction solution under the sample solution layer; the sample solution and the first reaction solution aspirated using the dispensing unit may be discharged to the second reaction solution to carry out the main reaction; and the amount of antigen may be measured by adding the third reaction solution containing a substrate solution and measuring the amount of luminescence.

As the fourth embodiment of the present invention, a sandwich ELISA method of an antigen, using a measuring apparatus equipped with a dispensing unit, using a whole blood sample solution containing a target substance (antigen); the first reaction solution containing an antibody labeled with alkaline phosphatase, and a free antibody which inhibits the formation of immunocomplex in the main reaction and which specifically reacts with the antigen; and the second solution containing an antibody which is immobilized on magnetic particles and which specifically reacts with the antigen, is exemplified. More particularly, the first step of aspirating the sample solution using the dispensing unit, and the second step of aspirating the first reaction solution using the dispensing unit may be carried out, to layer the first reaction solution under the sample solution layer; the sample solution and the first reaction solution aspirated using the dispensing unit may be discharged to the second reaction solution to carry out the main reaction; and the amount of antigen may be measured by adding the third reaction solution containing a substrate solution and measuring the amount of luminescence. In the main reaction, a competitive reaction between the immobilized antibody or the labeled antibody and the free antibody occurs against the antigen.

EXAMPLES

The present invention now will be further illustrated by, but is by no means limited to, the following Examples, which merely exemplify the present invention. Various changes and modifications obvious to those skilled in the art are possible without departing from the scope of the appended claims.

Example 1

Preparation of Reagents for Measuring C-Reactive Protein (CRP)

(1) Preparation of Samples

As samples, a whole blood sample and a plasma sample were provided. The plasma sample was prepared from the same sample by centrifuging the whole blood sample at 3000 rpm for 15 minutes at 8° C.

(2) Preparation of Magnetic Particle Solution

Magnetic particles (2.4 µm) were sensitized with an anti-CRP monoclonal antibody (CRP-1: Immuno Probe Co., Ltd.) in a 50 mmol/L MES buffer (pH 6.0), and stabilized in a Tris buffer (0.01 mol/L, pH 8.0) containing a 0.02% surfactant, to prepare anti-CRP-antibody-bound magnetic particles. The resulting magnetic particles were suspended into a 50 mmol/L MOPS buffer (pH 6.5) so that the concentration of the anti-CRP monoclonal antibody (CRP-1) became 0.3 mg/mL, and used.

(3) Preparation of Labeled Antibody Solution

An anti-CRP monoclonal antibody (CRP-4: Immuno Probe Co., Ltd.) was conjugated with bovine alkaline phosphatase (ALP) by a maleimide activated conjugation, to prepare an ALP-labeled anti-CRP antibody. The resulting labeled antibody was dissolved in a 20 mmol/L MES buffer (pH 6.0) containing 15% sucrose and 0.3 mg/mL anti-CRP monoclonal antibody (CRP-1), and used. A labeled antibody solution for comparison without sucrose was prepared in a similar fashion.

(4) Preparation of Washing Solution

A 10 mmol/L MES buffer (pH 6.5) containing 0.05% Triton X-100 and 0.9% NaCl was prepared.

(5) Preparation of Dilution Solution

A 0.1 mol/L MOPS buffer (pH 7.5) containing 1% bovine serum albumin (BSA) and 0.3 mol/L NaCl was prepared.

(6) Luminescent Substrate

As a luminescent substance, a 0.4 mmol/L CDP-Star solution (Applied Biosystems) was used.

Figure 2:
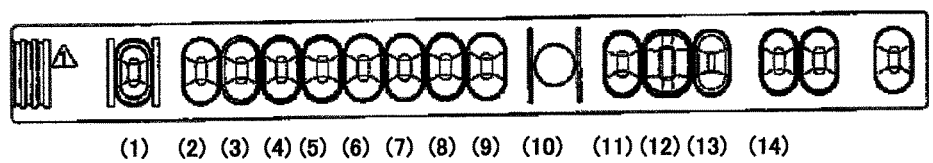
FIG. 2 is a plain view schematically showing a cartridge used in the Examples.

The resulting reagents were packaged in cartridges made of polypropylene (PP) as shown in FIG. 2, and an automated enzyme immunoassay analyzer (PATHFAST: Mitsubishi Chemical Medience Corporation) was used to carry out a measurement. Sample well (1), labeled antibody storage well (2), washing well 1 (3), washing well 2 (4), washing well 3 (5), magnetic particle storage well (7), dilution solution well (11), and substrate well (13) were filled with the reagents and the solutions prepared in Example 1(1) to Example 1(6), and the top of each reagent storage well was sealed with aluminum foil. The positions to be filled and the volumes of the reagents and solutions were as follows. The wells not specified were empty wells.

| | |
|---|---|
| Sample well (1) | 100 µL |
| Labeled antibody storage well (2) | 85 µL |
| Washing well 1 (3) | 400 µL |
| Washing well 2 (4) | 400 µL |
| Washing well 3 (5) | 400 µL |
| Magnetic particle storage well (7) | 50 µL |
| Dilution solution well (11) | 100 µL |
| Substrate well (13) | 140 µL |

Example 2

Measurement Process with Automated Analyzer

In Comparative Example 1 and Example 3 described below, CRP contained in samples was measured using the reagent cartridge prepared in Example 1 in accordance with the following steps described in this Example, using an automated analyzer (PATHFAST) equipped with 6-channel aspirating and discharging units and 6-channel magnetic particle separation units.

(1) Dispense 100 µL of sample into sample well (1) of the cartridge prepared in Example 1.

(2) Set the reagent cartridge into which the sample has been dispensed on the automated analyzer.

(3) Start the automated analyzer.

(4) The automated analyzer reads the barcode attached to the reagent cartridge, and recognizes that CRP is a subject to be measured.

(5) Punch a hole with a projection in the aluminum seal on the top of the reagent cartridge.

(6) Aspirate 50 µL of sample from sample well (1), and then aspirate 50 µL of dilution solution from dilution well (11), and discharge the whole into empty well (14). The first dilution step is carried out by repeated aspiration and discharge in empty well (14).

(7) Aspirate 50 µL of the mixed solution of the sample and the dilution solution from well (14), and then aspirate 50 µL of labeled antibody from labeled antibody storage well (2). Discharge the whole into magnetic particle storage well (7), to mix it with the magnetic particles and react them at 37° C. for 5 minutes.

(8) Separate the magnetic particles using a magnet in magnetic particle storage well (7).

(9) Wash the magnetic particles in washing well (3), and then separate the magnetic particles using a permanent magnet.

(10) Perform the operation of (9) in washing wells (4) and (5).

(11) Discharge the magnetic particles into substrate well (13) to mix them with the CDP-Star solution. After an enzyme reaction at 37° C. for 1 minute, measure the amount of luminescence using a photo multiplier tube (PMT) from the top of the photometric measuring well.

Comparative Example 1

Measurement of Whole Blood Sample and Plasma Sample Derived from the Same Sample-1

The whole blood sample and the plasma sample were measured, using the reagent without sucrose prepared in Example 1, in accordance with the method of Example 2. The plasma sample was prepared from the same sample by centrifuging the whole blood sample at 3000 rpm for 15 minutes at 8° C.

Figure 3:
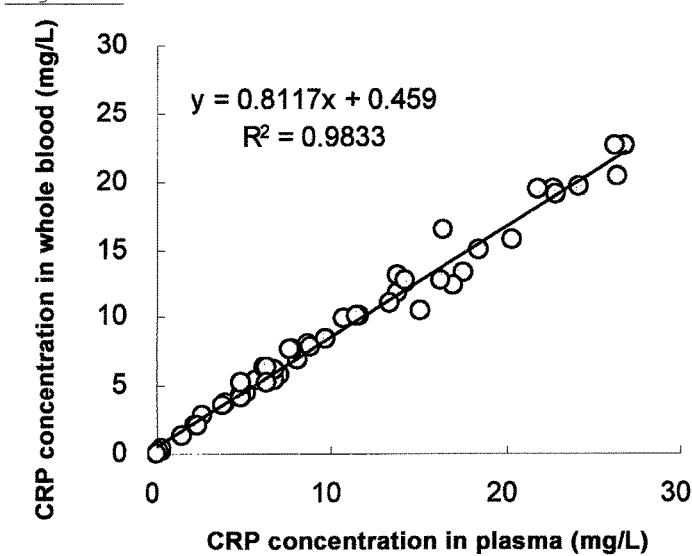
FIG. 3 is a graph showing the correlation between the measured values of whole blood and the measured values of plasma when the first reagent (labeled antibody reagent) does not contain a sugar (sucrose).
Figure 4:
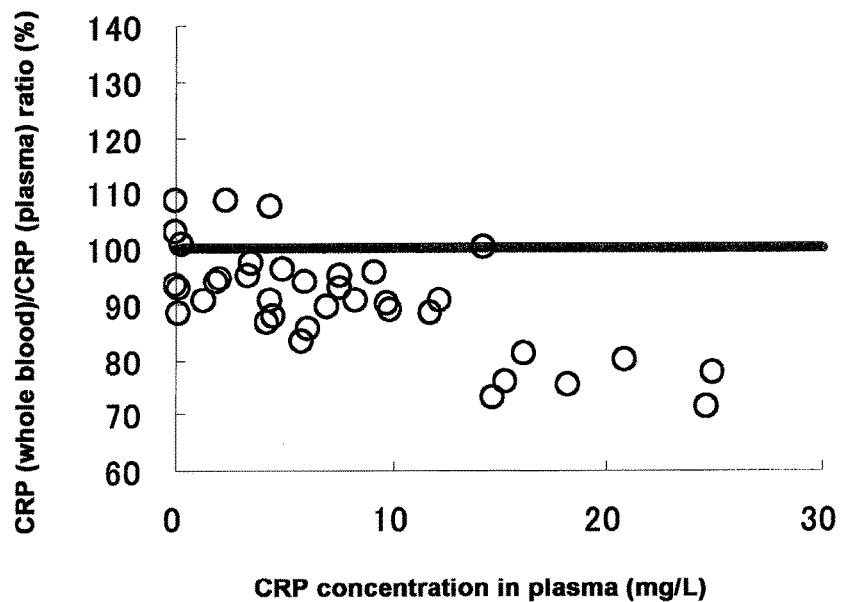
FIG. 4 is a graph showing the ratio of the measured values of whole blood to the measured values of plasma when it does not contain a sugar as shown in FIG. 3.

The results are shown in FIGS. 3 and 4. As apparent from FIG. 3, when sucrose was not added to the measurement system, with respect to the correlation between the measured values of the plasma sample and those of the whole blood sample, the slope was 0.8117, and approximately 20% divergence was observed. The ratios of the measured values of the plasma sample to the measured values of the whole blood sample (the measured values of the plasma sample÷the measured values of the whole blood sample) are shown in FIG. 4. As apparent from FIG. 4, although the theoretical ratio should be around 100%, it was confirmed that when the concentration became high, the ratio was widely spread.

Therefore, the present inventors examined the cause, and found that in the case of the whole blood sample, as shown in FIG. 1, the labeled antibody solution rose through the whole blood sample, and the reaction started. Further, the present inventors confirmed their specific gravities, the specific gravities of the plasma sample and the labeled antibody solution were almost similar to each other, and the specific gravity of the whole blood was 1.053 g/cm$^3$, and the specific gravity of the labeled antibody solution was 1.014 g/cm$^3$. The specific gravity of the labeled antibody solution was lower than that of the whole blood sample by approximately 3.7%, but it was found that a difference which significantly affected the reaction occurred.

Example 3

Measurement of Whole Blood Sample and Plasma Sample Derived from the Same Sample-2

Since it was found from the results of Comparative Example 1 that the cause was due to different specific gravities, the present inventors examined whether or not the problem could be solved under the conditions where the labeled antibody solution, of which the specific gravity became higher by using sucrose, was immiscible with the whole blood sample. The measurement was carried out in a similar fashion to that of Comparative Example 1, except that the sucrose-containing reagent prepared in Example 1 was used.

Figure 5:
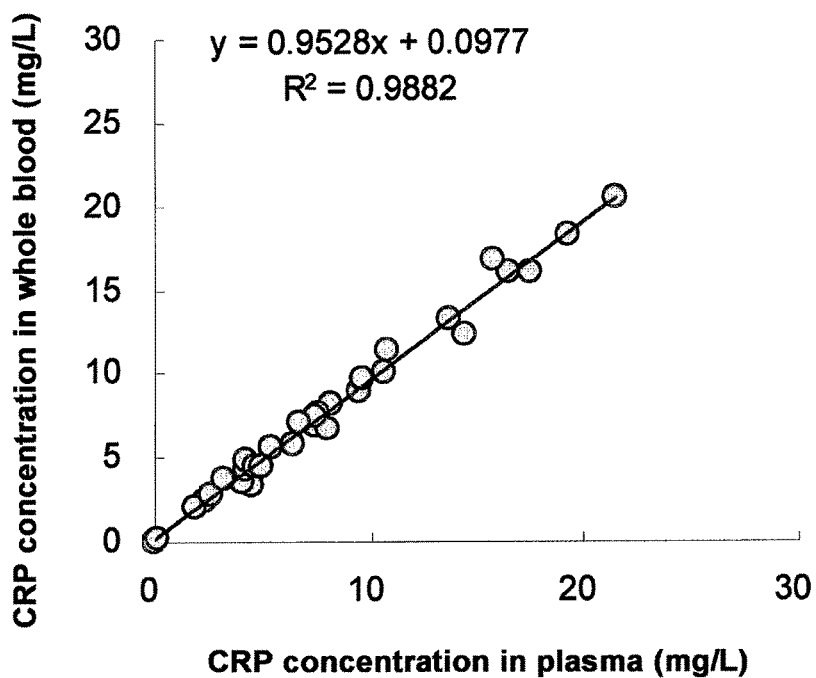
FIG. 5 is a graph showing the correlation between the measured values of whole blood and the measured values of plasma when the first reagent (labeled antibody reagent) contains 15% sucrose.
Figure 6:
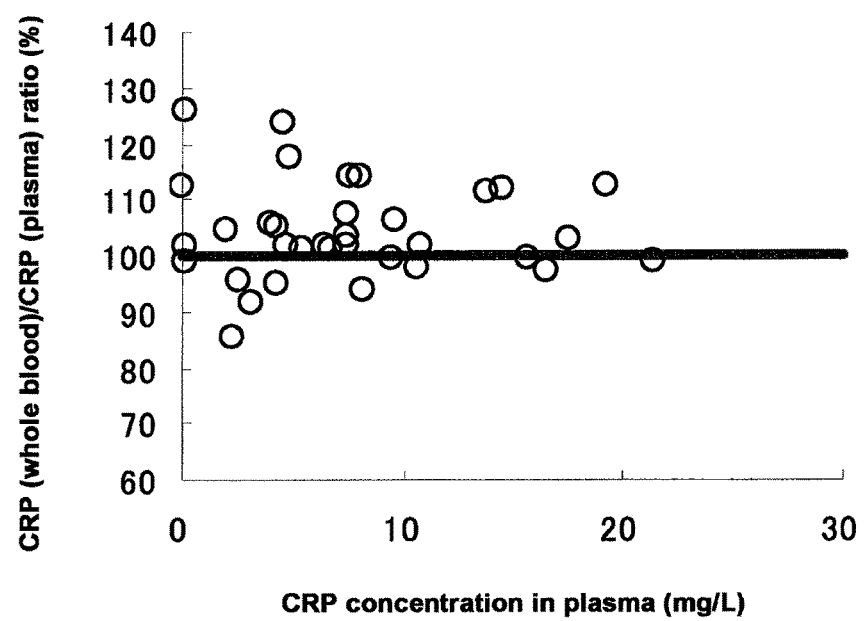
FIG. 6 is a graph showing the ratio of the measured values of whole blood to the measured values of plasma when it contains 15% sucrose as shown in FIG. 5.

The results are shown in FIGS. 5 and 6. As apparent from FIG. 5, when sucrose was added to the measurement system, with respect to the correlation between the measured values of the plasma sample and those of the whole blood sample, the slope was 0.9528, and the correlation was remarkably improved in comparison with the case that sucrose was not added. The ratios of the measured values of the plasma sample to the measured values of the whole blood sample (the measured values of the plasma sample÷ the measured values of the whole blood sample) are shown in FIG. 6. As apparent from FIG. 6, it was confirmed that the calculated ratios were located around 100%.

As described above, it was found that the divergence between the whole blood sample and the plasma sample can be reduced by regulating the specific gravity through the addition of sucrose to the measurement system, and as a result, a measurement with accuracy and high precision can be achieved.

Therefore, when the specific gravity is regulated by adding sucrose to the labeled antibody solution, the present inventors examined the difference needed between the labeled antibody solution and the whole blood sample solution in specific gravity.

As a result, when the specific gravity of the whole blood sample solution was approximately 1.053 g/cm$^3$: an addition of 5% sucrose as a final concentration to the sample solution resulted in a decreased change in the specific gravity of the sample solution after the addition with respect to the whole blood sample solution by approximately 2.18%; an addition of 10% sucrose as a final concentration resulted in an increase change by approximately 0.96%; an addition of 15% sucrose as a final concentration resulted in an increase change by approximately 1.5% to 2.56%; and an addition of 20% sucrose as a final concentration resulted in an increase change by approximately 7.5%, respectively. Therefore, the present inventors further examined, and found that when sucrose is added to the labeled antibody solution at a final concentration of 10% or more, the labeled antibody solution is immiscible with the whole blood sample, as described above, and the correlation between the measured values of the plasma sample and those of the whole blood sample can be obtained.

INDUSTRIAL APPLICABILITY

According to the present invention, it is possible to simultaneously start reactions which constitute the main reaction, and therefore, a target substance contained in a sample can be measured accurately and with high precision. Further, since a measurement with high precision can be carried out regardless of the type of sample, a convenient measurement without misuse can be carried out, and it can be said that the present invention is a measuring method with high availability.

Although the present invention has been described with reference to specific embodiments, various changes and modifications obvious to those skilled in the art are possible without departing from the scope of the appended claims.

The invention claimed is:

1. A method of measuring a target substance, comprising:
providing a sample suspected of containing the target substance, or a solution derived from the sample, a first reaction solution, and a second reaction solution;
aspirating the sample or the solution derived therefrom, and the first reaction solution, using a measuring apparatus equipped with a dispensing unit, sequentially in this order into the dispensing unit;
discharging the sample or the solution derived therefrom, and the first reaction solution at the same time from the dispensing unit, to bring the sample or the solution derived therefrom, and the first reaction solution into contact with the second reaction solution, and to form a complex of the target substance, a first partner which is contained in the first reaction solution and reacts specifically with the target substance, and a second partner which is contained in the second reaction solution and reacts specifically with the target substance; and
analyzing the complex, or a signal derived from the complex, wherein
the specific gravity of the first reaction solution is higher than the specific gravity of the sample or the solution derived therefrom;
the sample or the solution derived therefrom and the first reaction solution are aspirated into the dispensing unit in an overlaid state; and
the first partner, which is contained in the first reaction solution and reacts specifically with the target substance, is labeled with a labeling substance, and the second partner, which is contained in the second reaction solution and reacts specifically with the target substance, is immobilized on a solid-phase carrier selected from the group consisting of beads, magnetic particles, and latex particles.

2. The method according to claim 1, wherein the sample is whole blood.

3. The method according to claim 1, wherein the first partner which reacts specifically with the target substance is an antibody or an antigen.

4. The method according to claim 1, wherein the first partner which reacts specifically with the target substance is contained in the first reaction solution, and a second partner which recognizes a region different from a region recognized by the first partner and reacts specifically with the target substance is contained in the second reaction solution.

5. The method according to claim 1, wherein the dispensing unit is a tip.

6. The method according to claim 1, wherein the first reaction solution contains at least one substance selected from the group consisting of polyhydric alcohols, sugar alcohols, and sugars.

7. The method according to claim 6, wherein the first reaction solution contains at least one substance selected from the group consisting of ethylene glycol, propylene glycol, diethylene glycol, glycerol, pentose, hexose, triose, tetrose, heptose, sucrose, trehalose, isotrehalose, kojibiose, sophorose, nigerose, laminaribiose, maltose, cellobiose, isomaltose, gentiobiose, lactose, turanose, maltulose, palatinose, gentiobiulose, mannobiose, melibiose, melibiulose, neolactose, galactosucrose, scillabiose, rutinose, rutinulose, xylobiose, primellose, oligosaccharides, raffinose, melezitose, and maltotriose.

8. The method according to claim 6, wherein one or more substances described in claim 6 are included in the first reaction solution in an amount of 10% to 30% as the total amount thereof.

9. The method according to claim 1, wherein at least one of the first reaction solution or the second reaction solution contains a third partner which inhibits the formation of the complex with the target substance and reacts specifically with the target substance.

10. The method according to claim 9, wherein the third partner which reacts specifically with the target substance is an antibody or an antigen.

11. The method according to claim 9, wherein the first reaction solution and the second reaction solution contain the third partner which reacts specifically with the target substance.

12. The method according to claim 11, wherein the third partner which reacts specifically with the target substance is an antibody or an antigen.

* * * * *